(12) United States Patent
Shim et al.

(10) Patent No.: US 8,541,010 B2
(45) Date of Patent: Sep. 24, 2013

(54) COSMETIC COMPOSITION COMPRISING DOUBLE-SHELL NANO-STRUCTURE

(75) Inventors: Sung-Bo Shim, Seoul (KR);
Byoung-Young Jeon, Seoul (KR);
Joo-Hyuck Lim, Seoul (KR);
Jong-Keun Choi, Seoul (KR);
Yong-Joon Joo, Seoul (KR); Jin-Hun Cho, Seoul (KR)

(73) Assignee: Woongjin Coway Co., Ltd. (KR)

( * ) Notice: Subject to any disclaimer, the term of this patent is extended or adjusted under 35 U.S.C. 154(b) by 228 days.

(21) Appl. No.: 13/023,804

(22) Filed: Feb. 9, 2011

(65) Prior Publication Data

US 2012/0015011 A1 Jan. 19, 2012

(30) Foreign Application Priority Data

Jul. 13, 2010 (KR) ........................ 10-2010-0067350

(51) Int. Cl.
*A61K 8/02* (2006.01)
*A61K 36/00* (2006.01)

(52) U.S. Cl.
USPC ......................................... 424/401; 424/773

(58) Field of Classification Search
USPC ................................. 424/401, 773
See application file for complete search history.

(56) References Cited

FOREIGN PATENT DOCUMENTS

| JP | 2006-321763 | 11/2006 |
|---|---|---|
| WO | 2005/000258 | 1/2005 |

OTHER PUBLICATIONS

KR 10-2008-0041221 Machine Translation, 2008.*
KR 10-2007-0052564, Machine Translation, 2007.*

* cited by examiner

*Primary Examiner* — Blessing M Fubara
*Assistant Examiner* — Jennifer Berrios
(74) *Attorney, Agent, or Firm* — Cantor Colburn LLP (57) ABSTRACT

Disclosed is a cosmetic composition having a double-shell type nano-structure. More particularly, the nano-structure of the cosmetic composition includes: a water-soluble bioactive ingredient core; a core shell containing poly(ethyleneglycol)-poly(caprolactone)-poly(ethyleneglycol) (PE-PCL-PEG) tri-block copolymer in order to include the bioactive ingredient core therein; and an outer shell containing phospholipids or derivatives thereof in order to enclose the core shell therein. Such a cosmetic composition improves stability of active components which are prone to oxidation, light degradation, heat degradation, etc., is formed in a nanoparticle size which in turn shows high transdermal absorption and is very useful to prepare a cosmetic composition stably encapsulating various bioactive ingredients with anti-wrinkle effects, whitening effects, and so forth.

11 Claims, 3 Drawing Sheets

COSMETIC COMPOSITION COMPRISING DOUBLE-SHELL NANO-STRUCTURE

BACKGROUND OF THE INVENTION

1. Field of the Invention

The present invention relates a cosmetic composition including a double-shell nano-structure useful for production of cosmetic compositions wherein active ingredients having wrinkle reduction and/or whitening effects are stably encapsulated in the structure.

2. Description of the Related Art

Functional cosmetics are products providing various effects such as skin whitening, wrinkle reduction, artificial tanning, skin protection against UV light, etc. Some active ingredients as raw materials of these products, for example, retinol, vitamin A or C, etc., have disadvantages such as reduced stability when exposed to light, heat and/or air and decrease in skin absorption which in turn reduces cost effectiveness of the ingredients.

By stabilizing materials such as retinol, tocopherol, vitamin A or C used in cosmetics, physiologically active ingredients may be protected from the external environment. Also, enhanced skin affinity may enable easy absorption of such ingredients into the skin. As such, a great deal of research and development has focused on high performance cosmetics.

In order to realize such high performance cosmetics, primary requirements, development of bioactive materials with high performance and efficacy demonstrated in the art, assessment techniques to demonstrate efficacy of physiologically active (often bioactive) materials on the skin, techniques to correctly deliver desired functions of bioactive materials to a certain site of a human body, and so forth should be satisfied.

For embodiment of desired functions of a bioactive material with high performance, which is under continuous development, at a desired site of the human body, 'active targeting' to correctly deliver the active material to the site is of utmost importance. Accordingly, there is a strong requirement for development of improved processes to safely and stably deliver physiologically active materials with high performance to desired sites of a human body.

In order to solve the foregoing problems, development of biodegradable polymers with bio-affinity attracts attention in regard to research into stabilization of emulsions and transdermal delivery systems. However, owing to inherent characteristic of the cosmetics industry, such development requires contributions from a variety of different fields such as surface chemistry, biochemistry, dermatology, nanotechnology, polymer engineering, chemical engineering, etc., although still not accomplishing satisfactory results thereof.

SUMMARY OF THE INVENTION

Accordingly, the present invention is directed to solving the conventional problems described above. An object of the present invention is to provide a cosmetic composition having a nano-structure applicable to various functional cosmetics, wherein the nano-structure stably encases physiologically active ingredients, contains nanometer scale particles and provides enhanced skin absorption.

In order to achieve the foregoing object, the present invention provides a cosmetic composition having a nano-structure, wherein the nano-structure comprises:

a water-soluble core made of a bioactive ingredient ('bioactive ingredient core'); a core shell containing poly(ethyleneglycol)-poly(caprolactone)-poly(ethyleneglycol) (PEG-PCL-PEG) triblock copolymer in order to include the bioactive ingredient core; and an outer shell containing phospholipids and/or derivatives thereof in order to enclose the core shell therein.

The nano-structure of the present invention may increase stability of active ingredients which are prone to oxidation, light degradation, heat degradation, etc., is formed in a nano-particle size which facilitates transdermal absorption and is very useful for preparation of a cosmetic composition stably encapsulating various bioactive ingredients with anti-wrinkle effects, skin whitening effects, and so forth.

BRIEF DESCRIPTION OF THE DRAWINGS

The above and other objects, features and other advantages of the present invention will be more clearly understood from the following detailed description, taken in conjunction with the accompanying drawings, in which.

DETAILED DESCRIPTION OF THE PREFERRED EMBODIMENTS

In order to overcome a problem of stability of active ingredients with various functions when used in a cosmetic composition, for example, lotions, creams, facial essences, eye creams, makeup bases, foundations, etc., the present invention proposes a double shell nano-structure and provides formation of the nano-structure at nanometer scale in order to ensure acceleration of transdermal delivery of active ingredients.

Figure 1:
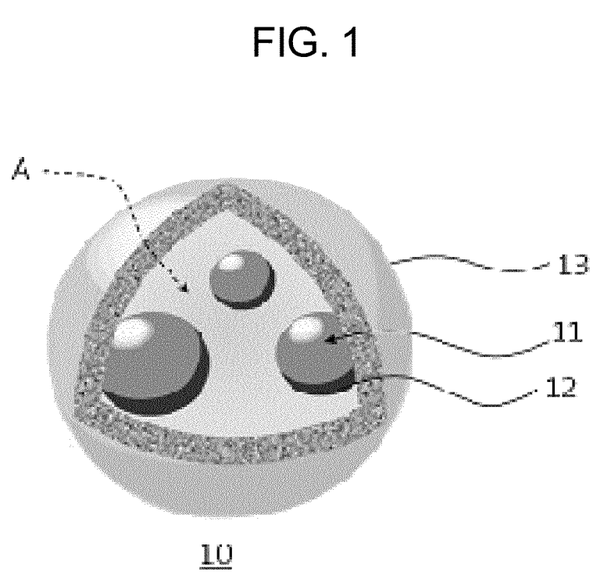
FIG. 1 is a three-dimensional cross-sectional view illustrating the construction of a nano-structure according to the present invention.

FIG. 1 is a three-dimensional cross-sectional view illustrating the construction of a nano-structure according to the present invention.

Referring to FIG. 1, a nano-structure 10 comprises: a water-soluble core 11 formed of bioactive ingredients ('bioactive ingredient core'); a core shell 12 surrounding the bioactive ingredient core 11 to include the same; and an outer shell 13 containing phospholipids or a derivative thereof in order to enclose the core shell 12 therein.

The bioactive ingredient core 11 which comprises a bioactive component to be introduced into particles in a cosmetic formulation may be prepared using bioactive materials commonly known in the art, in order to impart a certain efficacy or effect to a cosmetic product.

In particular, the bioactive ingredient core may be prepared using physiologically unstable active materials, which are typically used in preparation of cosmetics, for example, a skin whitening agent, a collagen biosynthesis promoter, an anti-wrinkle agent, a skin barrier enhancer, an ageing inhibitor, a moisturizer, etc.

Representative examples of a bioactive material with whitening effect may include a water-soluble component containing ascorbic acid 2-glucoside (AA2G), vitamin C (e.g., ascorbic acid), niacinamide, arbutine, Mulberry root extract, Broussonetia extract, magnesium ascorbyl phosphate, and the like. A bioactive material with anti-wrinkle effects may be a water-soluble component containing, for example, hydroxyproline, growth factors (EGF, FGF, IGF, etc.), peptides, N-acetyl glucosamine, and the like. The core shell 12 may contain a PEG-PCL-PEG triblock copolymer and such PEG-PCL-PEG triblock copolymer may comprise a hydrophilic polyethyleneglycol (PEG) A-block and a hydrophobic polycaprolactone (PCL) B-block. The foregoing triblock copolymer may be an ABA-type triblock copolymer having a certain relative molecular ratio of PEG:PCL:PEG ranging from 1:1:1 to 1:5:1, more preferably from 1:2:1 to 1:3:1. In addition, the triblock copolymer is preferably a biodegradable copolymer having an average molecular weight of 1,500 to 20,000 g/mol and a crystallization temperature $T_c$ of 10 to 40° C.

The triblock copolymer has crystalline property and, when used to prepare a cosmetic formulation, the triblock copolymer may be oriented on the surface of an emulsion to form a thin layer or film. Combination of the hydrophilic A-block and the hydrophobic B-block may induce simultaneous features of an amphiphilic surfactant with potential of self-assembly as well as an emulsifier. Such triblock copolymer may be easily adsorbed and oriented on the surface of an emulsion particle to form a thin layer or film during emulsification, so as to stabilize active but unstable ingredients contained in the particle. Moreover, the triblock copolymer may enable the emulsion particle to be easily absorbed and penetrated through a lipid double layer of an epidermal layer during transdermal penetration, owing to structural features of the emulsion particle, thereby improving functions of a cosmetic product containing the triblock copolymer. The triblock copolymer may be directly prepared and used or one commercially available on the market. The triblock copolymer has a variety of functional features depending on the design of various copolymer blocks, in particular, may be used as a surfactant, a transdermal penetration promoter, etc., and/or to improve stability of an emulsion system, enhance stability of unstable bioactive ingredients in particles, and so forth.

Especially, the present invention may enable fabrication of a nano-structure 10 containing nanometer scale particles using the outer shell 13. Korean Publication No. 2008-105249 discloses a particle including active ingredients prepared in the form of microparticles having a particle size of 17 to 20 μm, using a triblock copolymer. Since skin penetration increases as particle size decreases, transdermal penetration may be improved when particles are prepared at nanometer scale. Accordingly, the present invention enables production of nanometer scale particles from conventional microparticles, using an extremely high pressure emulsion system, during which the core shell 12 including the bioactive ingredient core 11 is further encased in phospholipids.

The outer shell 13 of the nano-structure 10 may comprise phospholipids or derivatives thereof, and surrounds the core shell 12 to encase the same.

Phospholipids that are structurally similar to lipids contained in skin may show excellent prevention of re-coagulation and skin affinity, and improve dispersive properties which in turn enhances color vividness while efficiently preventing dry skin. A preferred example of phospholipids used in the present invention is naturally-derived saturated lecithin extracted from soy beans or egg yolk. Such saturated lecithin may contain 23 to 95 wt. % of phosphatidylcholine and less than 20 wt. % of phosphatidyl ethanolamine. Furthermore, unsaturated choline compounds such as phosphatidylcholine, lysophosphatidylcholine or phosphatidyl ethanolamine as constituents of lecithin, serine compounds, ethanolamine compounds, and/or derivatives thereof including hydrogenated compounds may also be used.

The phospholipids may be included in an amount of 0.5 to 15.0 wt. % based on a total weight of the nano-structure. If this amount is below the lower limit, nanometer scale particles cannot be obtained. On the other hand, when phospholipid content exceeds the upper limit, a viscosity of a raw material and/or a prepared formulation is too high to desirably disperse and dissolve the same and to enable extra-high pressure emulsification using typical formulations and/or a high pressure homogenizer (e.g., micro-fluidizer), thus not producing desired formulations. As a result of measuring a particle size in Experimental Example 1 of the present invention, it was found that microparticles at a particle size of several tens of micrometers are prepared when phospholipid content is low.

Moreover, the outer shell 13 may comprise a co-emulsifier used together with phospholipids and such co-emulsifier may include, for example, anionic, cationic, non-ionic and/or amphoteric emulsifiers. Depending on contents of phospholipids and/or constituents of the co-emulsifier, the co-emulsifier may be added in an amount of 0.5 to 5 times, preferably 1 to 3 times of the content of phospholipids. Such co-emulsifier may include, for example: polyglyceryl compounds such as polyglyceryl-10-pentahydroxy stearate, polyglyceryl-2-isostearate, polyglyceryl-2-oleate, polyglyceryl-3-diisotearate, etc.; or silicon compounds such as cetyl dimethicone copolyol, dimethicone copolyol, etc., alone or in combination of two or more thereof.

Referring to FIG. 1, active ingredients useful in the present invention may be further introduced into a space A between the core shell 12 and the outer shell 13. As such active ingredients, compounds with anti-wrinkle effects and/or whitening effects as described above may be used.

Bioactive materials with skin whitening effects may include, for example, oil-soluble components such as oil-soluble licorice, ethyl ascrobyl ether, α-bisabolol, and the like. Alternatively, active compounds with anti-wrinkle effects may include, for example, oil-soluble components such as retinol and derivatives thereof (e.g., retinyl palmitate), adenosine, etc.

Addition of the foregoing active ingredients may be introduced in a process for inclusion of the water-soluble bioactive ingredient core 11 or a further inclusion process thereof within the outer shell 13.

According to a preferred embodiment of the present invention, a core shell may have the following constitutional composition, based on 100% by weight of the core shell:
 (i) 0.1 to 5.0 wt. % of water-soluble bioactive ingredient;
 (ii) 50.0 to 70.0 wt. % of oil;
 (iii) 0.5 to 20.0 wt. % of a triblock copolymer; and
 (iv) the remainder of water.

The nano-structure of the present invention may have the following constitutional composition, based on 100 wt. % of the nano-structure:
 (a) 0.5 to 20 wt. % of the core shell having water-soluble bioactive ingredients included therein;
 (b) an oil phase part including (i) 0.5 to 10.0 wt. % of oil and (ii) less than 5.0 wt. % of an oil-soluble active component; and
 (c) an aqueous phase part including (i) 0.5 to 15.0 wt. % of phospholipids, (ii) 10.0 to 60.0 wt. % of polyol, (iii) less than 5.0 wt. % of a water-soluble bioactive ingredient and (iv) the remainder of water.

The oil may be a commercially available oil capable of sufficiently dissolving bioactive ingredients and a surfactant therein. Particularly, the oil may be at least one selected from a group consisting of: hydrocarbon oils such as polydecene and paraffin oil; ester based synthetic oils; silicon oils; animal/vegetable oils; ethoxylated alkylester oils; cholesterol; cholesteryl sulfate; phytosphingosine; sphingoid lipid; $C_{10}$ to $C_{40}$ fatty alcohol; caprylic/capric triglyceride; ceramide; and mixtures thereof. Other than the oil, hydrocarbons as well as at least one fatty acid selected from a group consisting of: lauric acid; myristic acid; palmitic acid; stearic acid; oleic acid; linoleic acid; and mixtures thereof, may be further added to the nano-structure of the present invention.

The water used in the present invention may be distilled water, more preferably deionized distilled water.

The polyol used in the present invention is not particularly limited but may include any one commonly known in the art. The polyol may be at least one selected from a group consisting of: propyleneglycol; dipropyleneglycol; butyleneglycol; glycerin; methyl propanediol; isopreneglycol; pentyleneglycol; and mixtures thereof. The polyol is more preferably butyleneglycol or glycerin and most preferably butyleneglycol.

If required, any solvent or additive typically used in the art may be optionally added to the nano-structure. Such solvent acts to dissolve oil-soluble components and may include ethanol, propanol, butanol, and/or a mixture thereof. Such an additive may be at least one selected from a preservative, a pH adjuster, a surfactant, an antioxidant, a UV protector (or screener), a pigment, a dye, a perfume, a stabilizer, a thickener, etc. and can be appropriately selected by those skilled in the art.

A process for fabrication of a nano-structure according to the present invention is not particularly limited but may include any conventional emulsification method, and preferably a high pressure emulsification process. In particular, the inventive process comprises:

(S1) dissolving a water-soluble bioactive ingredient and a triblock copolymer in purified water and admixing the solution with an oil to prepare a core shell composition having the bioactive ingredient included in a core of the composition;

(S2) preparing an oil phase part that contains oil and optionally an oil-soluble active component, as well as an aqueous phase part that contains phospholipids, polyol and optionally a water-soluble bioactive component dissolved in water; and (S3) adding the core shell composition of S1 and the oil phase part of S2 to the aqueous phase part and treating the mixture via extremely high pressure emulsification, so as to produce the nano-structure.

Such dissolution may be executed by any conventional method and optionally under agitation or while heating the same at 50 to 80° C., preferably 65 to 75° C.

Emulsification may be performed using a typical mixer (e.g., a homo-mixer) to agitate the mixture preferably at 2000 to 4000 rpm, more preferably at 3000 rpm for 3 to 10 minutes, in order to produce a first emulsified product.

The first emulsified product is cooled to 50 to 60° C., followed by further emulsification three times, using a high pressure homogenizer or emulsifier at 500 bar, preferably 1000 to 2500 bar, thereby fabricating a nano-structure.

The prepared nano-structure may include nanometer scale particles and be provided as an emulsion. The core having the water-soluble bioactive ingredients included therein has a particle size of 80 to 110 nm, while the outer shell containing phospholipids has a particle size of 300 to 350 nm. Furthermore, the nano-structure having the outer shell and the core encased therein may have a particle size of 300 to 500 nm, preferably 390 to 460 nm (see FIG. 2). That is, the nano-structure with such a particle size range is substantially formed at nanometer scale, compared to micro-emulsion particles commonly known in the art. Therefore, when applied to the skin, a surface area in contact with the skin may be relatively increased, which in turn improves transdermal penetration and increases a transdermal penetration area.

In consideration that a gap between intercellular lipids of skin stratum corneum is about 50 nm and an emulsion membrane of an emulsion particle shows flexibility, the inventive nano-structure may have advantages in that skin micro-emulsion particles are absorbed into the intercellular lipids, thereby being easily dispersed.

In other words, the nano-structure of the present invention formed with an average nanoscale particle size may remarkably increase transdermal penetration of bioactive ingredients with excellent anti-wrinkle and whitening effects, wherein such active ingredients are included in a core of the nano-structure, via two routes of increase in contact area to skin and penetration/dispersion of emulsion particles into intercellular lipids.

The foregoing nano-structure of the present invention may be applied to a cosmetic composition and other high performance cosmetics.

When used in preparation of a cosmetic composition, a content of the nano-structure may range from 0.001 to 30.0 wt. %, preferably 0.1 to 5.0 wt. % based on a total weight of the cosmetic composition. If the content of the nano-structure is below the lower limit of this range, desired effects may not be achieved. On the other hand, if the content of the nano-structure exceeds the upper limit of this range, desired effects are not remarkably improved in proportion to such increase in content, and stability of a formulation having the nano-structure is deteriorated.

The cosmetic composition according to the present invention may be prepared in any one of formulations commercially available in the art, more preferably, solution, suspension, emulsion, paste, gel, cream, lotion, powder, soap, surfactant-containing cleansing formulations, oil, powdery foundation, emulsifying foundation, wax foundation, spray, etc.

Such a formulation may include various substrates and additives suitably required for fabrication of the formulation. Other typical compounds, for example, nonionic surfactants, silicon polymers, extender pigments, perfumes, antiseptics, fungicides, oxidation inhibitors, organic solvents, ionic or nonionic thickeners, skin softeners, antioxidants, free-radical scavengers, opacity providers, stabilizers, emollients, silicone, α-hydroxy acid, defoamers, moisturizers, vitamins, insect repellents, fragrances, preservatives, anti-inflammatory agents, substance P antagonists, fillers, polymers, propellants, basic agents, acidic agents, coloring agents, and so forth may further be added in an amount at which desired effects of the formulation are not decreased.

The following examples will be given to describe preferred embodiments of the present invention in detail. However, those skilled in the art will appreciate that various modifications, additions and substitutions of the foregoing embodiments are possible and it is not construed that the scope of the present invention is restricted to these examples. Briefly, the inventive examples have been disclosed for illustrative purposes for those who have common knowledge in the art to which the present invention pertains to more clearly understand the present invention.

EXAMPLES 1 TO 2 AND COMPARATIVE EXAMPLES 1 to 5

(1) Preparation of Core Shell

Raw materials with constitutional compositions and contents listed in Table 1 were prepared.

After heating an aqueous phase part and an oil phase part to 50° C. and completely dissolving the same, the oil phase part was slowly added to the aqueous phase part. Emulsifying the mixture using a homo-mixer at 2000 rpm for 3 minutes resulted in an emulsion containing first core shells. Triblock copolymer used in this process had a relative PEG:PCL:PEG ratio of 1:2:1 and was prepared using PEG and PCL, each having a molecular weight of 1,000 g/mol (according to a procedure described in Korean Publication No. 2008-0105249).

TABLE 1

Composition of Core shell

| | Name of raw material (wt. %) | Practical composition 1 | Comparative composition 1 |
|---|---|---|---|
| Aqueous phase | Purified water | 40 | 40 |
| | Triblock copolymer | 15 | — |
| | AA2G | 2.0 | 2.0 |
| | Vitamin C | 2.0 | 2.0 |
| | Mulberry root extract | 2.0 | 2.0 |
| Oil phase | Triglyceride | To 100 | To 100 |

(2) Preparation of Nano-structure

With the raw materials having certain constitutional compositions and contents listed in Table 1, a nano-structure including the core shell formed as described above was prepared.

Figure 2:
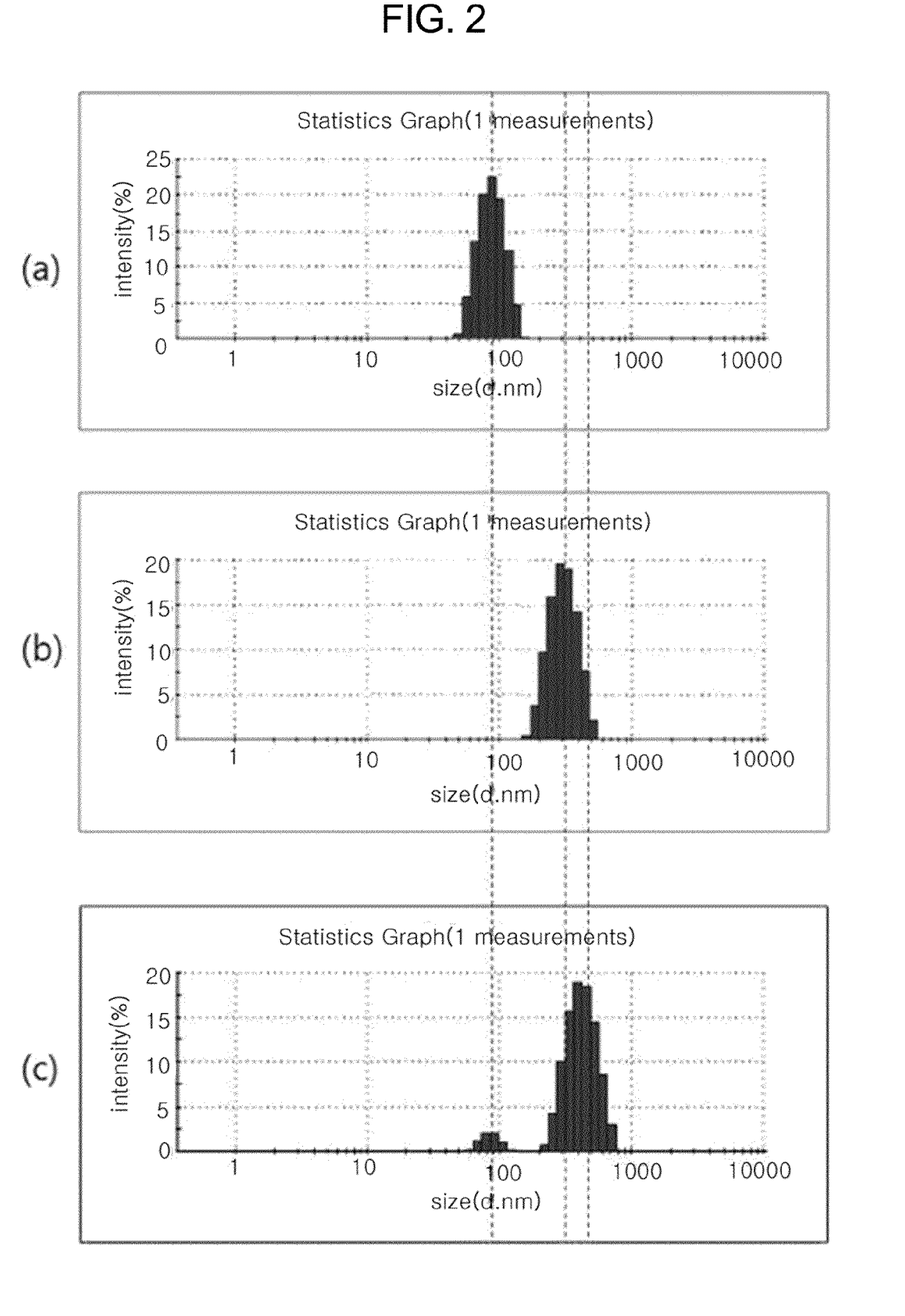
FIG. 2 shows a particle size distribution of an emulsion prepared in Example 1, especially, particle size distributions of (a) a core shell, (b) an outer shell and (c) a nano-structure.

After heating an aqueous phase part and an oil phase part to 70° C. and completely dissolving the same, the oil phase part was slowly added to the aqueous phase part. Emulsifying the mixture using a homo-mixer at 3000 rpm for 5 minutes resulted in an emulsion. The prepared emulsion was cooled to 45° C. and the emulsion prepared according to (1) was added dropwise to the cooled emulsion, followed by mixing at 2000 rpm for 5 minutes. Then, emulsification was conducted using a micro-fluidizer at 1,000 bar/3 cycles, so as to produce a final emulsion having the nano-structure dispersed therein.

size of the nano-structure according to the present invention ranged from 390 to 460 nm. Referring to FIG. 2(c), some core shells not included in the outer shells were observed at about 90 nm and removed through filtration.

On the other hand, an emulsion according to Comparative Example 1 has a particle size of about 15 μm while another emulsion according to Comparative Example 2 (Korean Publication No. 2007-105249) has a particle size of about 18 μm. Compared to these results, it is demonstrated that the present invention can produce an emulsion containing nanoscale particles.

According to Comparative Examples 3 and 4, emulsions and micro-particles (10 to 30 μm) were prepared. In particular, in Comparative Example 5, since viscosity is considerably high due to excess lecithin, an emulsion formulation could not be produced.

EXPERIMENTAL EXAMPLE 2

Assessment of Skin Penetration Accelerating Effect

Modified Franz diffusion cells were used to determine release amount of a drug based on a nano-structure having biodegradable triblock copolymer. The inventive nano-structure prepared using a biodegradable triblock copolymer containing AA2G and a typical emulsion containing AA2G, respectively, were applied to a skin specimen with a size of 4 cm² harvested from a rat. Then, the harvested specimen was fixed between a donor and a receptor phase and, in this case, the receptor phase was prepared using a phosphate buffer at pH 7.4 which was preheated to 37° C. A volume of the cell was 11 ml, test temperature was 37° C.±0.5° C. and an agitation speed was 600 rpm, and these conditions were continuously maintained.

TABLE 2

| | Raw material | Example 1 | Example 2 | Comparative Example 1 | Comparative Example 2 | Comparative Example 3 | Comparative Example 4 | Comparative Example 5 |
|---|---|---|---|---|---|---|---|---|
| Aqueous phase part in outer shell | Purified water | To 100 | To 100 | — | — | To 100 | To 100 | To 100 |
| | butyleneglycol | 30 | 30 | — | — | 30 | 30 | 30 |
| | Lecithin | 3.0 | 10 | — | — | — | 0.1 | 20 |
| Oil phase part in outer shell | Mineral oil | 5.0 | 5.0 | — | — | 5.0 | 5.0 | 5.0 |
| | Retinol | 1.0 | 1.0 | — | — | 1.0 | 1.0 | 1.0 |
| Core shell | Practical composition 1 | 10 | 10 | — | 100 | 10 | 10 | 10 |
| | Comparative composition 1 | — | — | 100 | — | — | — | — |

EXPERIMENTAL EXAMPLE 1

Measurement of Particle Size

Using a dynamic light scattering device (DLS), a particle size of the prepared nano-structure was measured. Results thereof are shown in FIG. 2.

FIG. 2 shows a particle size distribution of an emulsion prepared in Example 1, especially, particle size distributions of (a) a core shell, (b) an outer shell and (c) a nano-structure. Referring to FIG. 2, it can be seen that the core shell and the outer shell have particle size distributions ranging from 80 to 110 nm and from 300 to 350 nm, respectively. Also, a particle 1 ml was taken every 20 minutes for 5 hours using a micro-pipette for 5 hours and subjected to measurement of AA2G concentration through HPLC. Measured results are shown in FIG. 3.

Figure 3:
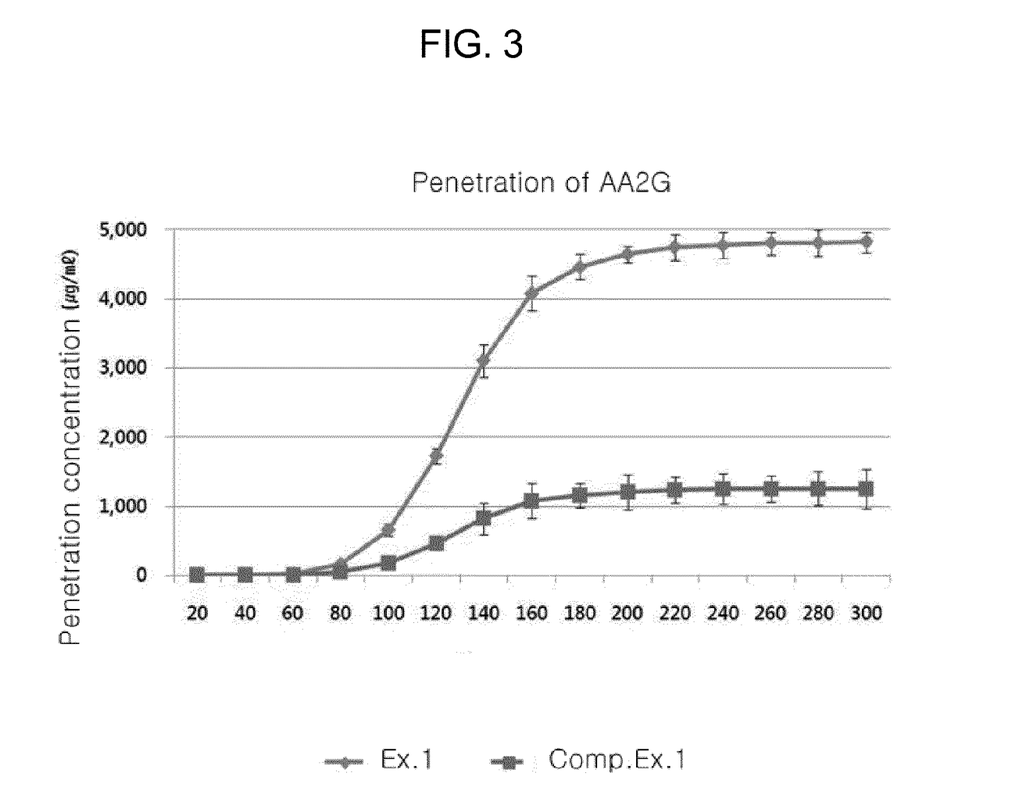
FIG. 3 is graphs illustrating results of skin penetration of emulsions prepared in Example 1 and Comparative Example 1, respectively.

FIG. 3 shows graphs for results of skin penetration of emulsions prepared in Example 1 and Comparative Example 1, respectively. Referring to FIG. 3, it can be seen that the inventive nano-structure can rapidly penetrate the skin and skin absorption speed was improved about 4.5 fold, 200 minutes after skin penetration, compared to the typical emulsion.

EXPERIMENTAL EXAMPLE 3

Assessment of Enhanced Stability

Each of the compositions prepared according to Examples and Comparative Examples was stored in an oven at 25° C., 5° C., 'cycle' and 45° C. for 1 month, followed by naked eye observation. In this regard, 'cycle' means that the composition was cyclically stored at 25° C., 5° C. and 45° C. for 6 hours at each temperature. In Table 3, '⊚' is excellent, '○' is good, 'Δ' is poor, and 'x' is very poor.

TABLE 3

|  | 45° C. | Cycle | 25° C. | 5° C. |
|---|---|---|---|---|
| Example 1 | ⊚ | ⊚ | ⊚ | ⊚ |
| Example 2 | ⊚ | ⊚ | ⊚ | ⊚ |
| Comparative Example 1 | ○ | ○ | ○ | ○ |
| Comparative Example 2 | ○ | ○ | ○ | ○ |
| Comparative Example 2 | ○ | ○ | ○ | ○ |
| Comparative Example 2 | ○ | Δ | ○ | ○ |
| Comparative Example 2 | ○ | ○ | Δ | Δ |

Referring to Table 3, it can be seen that both the inventive compositions prepared in Examples as well as other compositions prepared in Comparative Examples show favorable dispersion stability at relatively high or low temperatures.

Hereinafter, preferred formulations will be given in order to provide a clearer understanding of the present invention. However, these formulations are only proposed for illustrative purposes to support understanding of the present invention and the present invention is not restricted thereto.

FORMULATION EXAMPLE 1

Skin Softener (Skin Lotion)

As shown in Table 4, a skin softener was produced according to a conventional preparation method.

TABLE 4

| Ingredients | Content (wt. %) |
|---|---|
| Nano-structure in Example 1 | 2.0 |
| Glycerin | 5.0 |
| 1,3-butyleneglycol | 3.0 |
| PEG 1500 | 1.0 |
| Allantoin | 0.1 |
| DL-Panthenol | 0.3 |
| EDTA-2Na | 0.02 |
| Benzophenone-9 | 0.04 |
| Sodium hyaluronate | 5.0 |
| Ethanol | 10.0 |
| Octyldodeces-16 | 0.2 |
| Polysorbate 20 | 0.2 |
| Unicide-U 13 | 0.01 |
| Distilled water | The balance |
| Total | 100 |

FORMULATION EXAMPLE 2

Skin Toner

As shown in Table 5, a skin toner was produced according to a conventional preparation method.

TABLE 5

| Ingredients | Content (wt. %) |
|---|---|
| Nano-structure in Example 1 | 2.0 |
| Glycerin | 2.0 |
| 1,3-butyleneglycol | 2.0 |
| Allantoin | 0.2 |
| DL-Panthenol | 0.2 |
| EDTA-2Na | 0.02 |
| Benzophenone-9 | 0.04 |
| Sodium hyaluronate | 3.0 |
| Ethanol | 15.0 |
| Polysorbate 20 | 0.3 |
| Witch Hazel leaf extract | 2.0 |
| Citric acid | Trace |
| Unicide-U 13 | 0.01 |
| Distilled water | The balance |
| Total | 100 |

FORMULATION EXAMPLE 3

Facial Lotion

As shown in Table 6, a facial lotion was produced according to a conventional preparation method.

TABLE 6

| Ingredients | Content (wt. %) |
|---|---|
| Nano-structure in Example 1 | 2.0 |
| Glyceryl stearate SE | 1.5 |
| Cetearyl alcohol | 1.5 |
| Lanolin | 1.5 |
| Polysorbate 60 | 1.3 |
| Sorbitan stearate | 0.5 |
| Hydrogenated vegetable oil | 1.0 |
| Mineral oil | 5.0 |
| Squalane | 3.0 |
| Trioctanoin | 2.0 |
| Dimethicone | 0.8 |
| Tocopherol acetate | 0.5 |
| Carboxyvinyl polymer | 0.12 |
| Glycerin | 5.0 |
| 1,3-butyleneglycol | 3.0 |
| Sodium hyaluronate | 5.0 |
| Triethanolamine | 0.12 |
| Unicide-U 13 | 0.02 |
| Distilled water | The balance |
| Total | 100 |

FORMULATION EXAMPLE 4

Facial Cream

As shown in Table 7, a facial cream was produced according to a conventional preparation method.

TABLE 7

| Ingredients | Content (wt.%) |
|---|---|
| Nano-structure in Example 1 | 2.0 |
| Lipophilic glycerin monostearate | 2.0 |
| Cetearyl alcohol | 2.2 |
| Stearic acid | 1.5 |
| Beeswax | 1.0 |
| Polysorbate 60 | 1.5 |
| Sorbitan stearate | 0.6 |
| Hydrogenated vegetable oil | 1.0 |
| Squalane | 3.0 |
| Mineral oil | 5.0 |

TABLE 7-continued

| Ingredients | Content (wt.%) |
| --- | --- |
| Trioctanoin | 5.0 |
| Dimethicone | 1.0 |
| Sodium magnesium silicate | 0.1 |
| Glycerin | 5.0 |
| Betaine | 3.0 |
| Triethanolamine | 1.0 |
| Sodium hyaluronate | 4.0 |
| Unicide-U 13 | 0.02 |
| Distilled water | The balance |
| Total | 100 |

FORMULATION EXAMPLE 5

Massage Cream

As shown in Table 8, a massage cream was produced according to a conventional preparation method.

TABLE 8

| Ingredients | Content (wt. %) |
| --- | --- |
| Nano-structure in Example 1 | 2.0 |
| Lipophilic glycerin monostearate | 1.5 |
| Cetearyl alcohol | 1.5 |
| Stearic acid | 1.0 |
| Polysorbate 60 | 1.5 |
| Sorbitan stearate | 0.6 |
| Isostearyl isostearate | 5.0 |
| Squalane | 5.0 |
| Mineral oil | 35.0 |
| Dimethicone | 0.5 |
| Hydroxyethyl cellulose | 0.12 |
| Glycerin | 6.0 |
| Triethanolamine | 0.7 |
| Unicide-U 13 | 0.02 |
| Distilled water | The balance |
| Total | 100 |

FORMULATION EXAMPLE 6

Essence

As shown in Table 9, a facial essence was produced according to a conventional preparation method.

TABLE 9

| Ingredients | Content (wt. %) |
| --- | --- |
| Nano-structure in Example 1 | 2.0 |
| Glycerin | 10.0 |
| Betaine | 5.0 |
| PEG 1500 | 2.0 |
| Allantoin | 0.1 |
| DL-panthenol | 0.3 |
| EDTA-2Na | 0.02 |
| Benzophenone-9 | 0.04 |
| Hydroxylethyl cellulose | 0.1 |
| Sodium hyaluronate | 8.0 |
| Carboxyvinyl polymer | 0.2 |
| Triethanolamine | 0.18 |
| Octyldodecanol | 0.3 |
| Octyldodeces-16 | 0.4 |
| Ethanol | 6.0 |
| Unicide-U 13 | 0.01 |
| Distilled water | The balance |
| Total | 100 |

FORMULATION EXAMPLE 7

Massage Pack

As shown in Table 10, a massage pack was produced according to a conventional preparation method.

TABLE 10

| Ingredients | Content (wt. %) |
| --- | --- |
| Nano-structure in Example 1 | 2.0 |
| Polyvinylalcohol | 15.0 |
| Cellulose gum | 0.15 |
| Glycerin | 3.0 |
| PEG 1500 | 2.0 |
| DL-panthenol | 0.4 |
| Allantoin | 0.1 |
| Monoammonium glycyrrhizinate | 0.3 |
| Nicotinamide | 0.5 |
| Ethanol | 6.0 |
| PEG 40 hydrogenated castor oil | 0.3 |
| Unicide-U 13 | 0.02 |
| Distilled water | The balance |
| Total | 100 |

As is apparent from the foregoing, the nano-structure of the present invention may be used in a variety of cosmetic compositions including, for example, lotions, creams, eye creams, anti-wrinkle products, skin whitening products, sun screens, makeup bases, foundations, cosmetics for lips, and so forth.

What is claimed is:

1. A cosmetic composition comprising a nano-structure, wherein the nano-structure comprises:
   at least two core shell compositions comprising a water-soluble bioactive ingredient core and a core shell surrounding the bioactive ingredient core, wherein the bioactive ingredient core comprises a water-soluble bioactive ingredient and wherein
   the core shell comprises a poly(ethyleneglycol)-poly(caprolactone)-poly(ethyleneglycol) (PEG-PCL-PEG) triblock copolymer
   an outer shell comprising phospholipids, wherein the at least two core shell compositions are enclosed within the outer shell; and
   a space between the at least two core shell compositions and the outer shell, wherein the space comprises an oil-soluble bioactive component.

2. The cosmetic composition according to claim 1, wherein the water-soluble active ingredient includes at least one selected from a group consisting of ascorbic acid 2-glucoside (AA2G), vitamin C (ascorbic acid), niacinamide, arbutine, Mulberry root extract, Broussonetia extract, magnesium ascorbyl phosphate, hydroxyproline, growth factor, peptides, N-acetyl glucosamine, and mixtures of at least two or more thereof.

3. The cosmetic composition according to claim 1, wherein the triblock copolymer has a crystallization temperature $T_c$, of 10 to 40° C. and a relative ratio of PEG:PCL:PEG ranging from 1:1:1 to 1:5:1, and is prepared using PEG and PCL each having a molecular weight of 400 to 3,000 g/mol.

4. The cosmetic composition according to claim 1, wherein the phospholipids include at least one selected from a group consisting of: naturally-derived saturated lecithin extracted from soybean or egg yolk; unsaturated choline compounds such a phosphatidylcholine, lysophosphatidylcholine, phosphatidyl ethanolamine; serine compounds; ethanolamine compounds; and combinations of two or more thereof.

5. The cosmetic composition according to claim 1, wherein the phospholipids are present in an amount of 0.5 to 15.0 wt. % based on a total weight of the nano-structure.

6. The cosmetic composition according to claim 1, wherein the nano-structure comprises:
 (a) 0.5 to 20 wt. % of the at least two core shell compositions;
 (b) an oil phase part including (i) 0.5 to 10.0 wt. % of oil and (ii) less than 5.0 wt. % of an oil-soluble active component; and
 (c) an aqueous phase part including (i) 0.5 to 15.0 wt. % of phospholipids, (ii) 10.0 to 60.0 wt. % of polyol, (iii) less than 5.0 wt. % of a water-soluble bioactive ingredient and (iv) the remainder of water,
 wherein the weight percents are based on 100 wt. % of the nano-structure, and wherein the oil phase part and the aqueous phase part are present in the outer shell.

7. The cosmetic composition according to claim 6, wherein the core shell composition comprises:
 (i) 0.1 to 5.0 wt. % of a water-soluble bioactive ingredient;
 (ii) 50.0 to 70.0 wt. % of oil;
 (iii) 0.5 to 20.0 wt. % of a triblock copolymer; and
 (iv) the remainder of water, wherein the weight percents are based on 100 wt. % of the core shell composition.

8. The cosmetic composition according to claim 1, wherein the oil-soluble bioactive component comprises at least one of an oil-soluble licorice, ethyl ascorbyl ether, α-bisabolol, retinol, adenosine, and a combination of two or more thereof.

9. The cosmetic composition according to claim 1, wherein the nano-structure has an average particle diameter of 300 to 500 nm.

10. The cosmetic composition according to claim 1, wherein the cosmetic composition comprises 0.001 to 30.0 wt. % of the nanostructure based on a total weight of the cosmetic composition.

11. The cosmetic composition according to claim 1, wherein the cosmetic composition is produced in any one of formulations including skin softener, skin toner, facial lotion, facial cream, massage cream, facial essence and massage pack.

* * * * *